(12) United States Patent
Hashimoto et al.

(10) Patent No.: US 8,552,295 B2
(45) Date of Patent: Oct. 8, 2013

(54) CABLE ASSEMBLY

(75) Inventors: Takashi Hashimoto, Kanuma (JP);
Yunfei Zhu, Kanuma (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 461 days.

(21) Appl. No.: 13/048,723

(22) Filed: Mar. 15, 2011

(65) Prior Publication Data

US 2011/0232964 A1     Sep. 29, 2011

(30) Foreign Application Priority Data

Mar. 29, 2010   (JP) ................... 2010-075823

(51) Int. Cl.
*H02G 15/02* (2006.01)
(52) U.S. Cl.
USPC .......... 174/74 R; 174/75 F; 174/75 C; 174/78
(58) Field of Classification Search
USPC ........................................ 174/74 R, 75 F, 78
See application file for complete search history.

(56) References Cited

U.S. PATENT DOCUMENTS

| 4,739,126 A * | 4/1988 | Gutter et al. ................... 174/78 |
| 7,201,598 B2 * | 4/2007 | Griffin ......................... 439/352 |
| 2003/0082942 A1 * | 5/2003 | Wlos ............................ 439/348 |

FOREIGN PATENT DOCUMENTS

JP        H10-286228 A    10/1998

* cited by examiner

*Primary Examiner* — William H Mayo, III
(74) *Attorney, Agent, or Firm* — Global IP Counselors, LLP

(57) ABSTRACT

A cable assembly has a clamp provided at an end of a multi-core cable. The clamp, which is formed such that the inner diameter thereof increases as it is closer to the rear end, is fixed by caulking to the outer circumference of a sheath. An inner spring and an outer spring are arranged around the outer circumference of a sheath. The inner spring is fixed to the clamp in such a manner as the end thereof on the cable tip side is sandwiched between the sheath and the inner surface of the clamp. The outer spring is shorter than the inner spring in the cable axial direction, and the end thereof on the cable tip side is fixed to the outer circumference of the clamp. The outer circumference of the inner spring and the outer spring is covered with a rubber boot.

4 Claims, 5 Drawing Sheets

CABLE ASSEMBLY

BACKGROUND OF THE INVENTION

1. Field of the Invention

The present invention relates to a cable assembly having a clamp attached to a multi-core cable.

2. Description of the Background Art

Japanese Patent Application Publication No. H10-286228 describes a camera cable used for electrical relay between a control unit and an image capturing unit connected to an endoscope ocular part for performing monitor-observation. At a part where the camera cable is connected to a connector, a breakage prevention part consisting of an elastic member is provided for improving bending resistance of the cable.

A cable used for connection with equipment such as a camera, an ultrasonic probe, or the like is in some cases structured such that core wires contained in the cable are connected with a connector provided on the cable side while such connector is to be coupled with a connector provided on the equipment side. In such case, the cable is frequently bent at the vicinity of a connection portion, where core wires are connected with the connector provided on the cable side, and consequently the core wires within the sheath of the cable tend to move, often causing wire breakage or other like problems at an early stage for use. It is required that such a cable have bending resistance sufficient to withstand repeated bending for tens of thousands times, for example.

SUMMARY OF THE INVENTION

The object of the present invention is to provide a cable assembly having bending resistance that is sufficient to prevent a core wire from breaking even if the cable assembly is bent tens of thousands times at a position near the part where a clamp is attached.

To achieve the object, provided is a cable assembly comprising a multi-core cable, a cylindrical clamp, two layers of springs, and a rubber boot. In the cable assembly, the multi-core cable includes a bundled plurality of core wires having each conductor covered with an insulation, a shielding layer provided around the plurality of core wires, and a sheath formed around the shielding layer. The clamp is fixed to the sheath by clamping at an end of the multi-core cable in a state where the multi-core cable is inserted in the clamp, whereas at a position opposite to the front end of the multi-core cable, the clamp has a diameter increasing portion such that the inside diameter increases as it is closer to the rear end. The two layered springs include an inner spring and an outer spring. The inner spring, in which the multi-core cable is inserted, is attached around the sheath on the rear side of the clamp in such a manner as the spring end on the front side of the multi-core cable is fixed to the clamp in a state where it is held between the sheath and the internal circumference of the clamp. The outer spring, which is shorter than the inner spring in terms of the longitudinal direction of the multi-core cable, is provided in a manner such that the spring end on the front side of the multi-core cable is fixed to the outer circumference of the clamp. The rubber boot covers the outer circumferences of the inner spring and the outer spring.

In the cable assembly of the present invention, preferably the clamp has, as named from its tip side, a brim portion, a groove portion, a caulking portion, and a diameter increasing portion, and the rubber boot is fastened to the groove portion. Also, in the cable assembly of the invention, the inner spring and the outer spring are shaped in a cylindrical form by transforming a thin metal plate spirally or by making a spiral slit in a circular metal cylinder, and their spiral directions are opposite to each other.

According to the cable assembly of the present invention, even if the multi-core cable that is inserted in the clamp is repeatedly subjected to bending, it is possible to reduce the degree of mutual interference between the multi-core cable and the clamp and to moderate the bending angle of the inner core wires. Also, the two layered springs reinforce the part that will be subjected to such bending, and protects the sheath. Thus, according to these effects, it is possible to obtain such a high bending resistance as will not cause a core wire to break even if it is bent tens of thousands times in the vicinity of the part to which the clamp is attached.

DETAILED DESCRIPTION OF THE INVENTION

Figure 1:
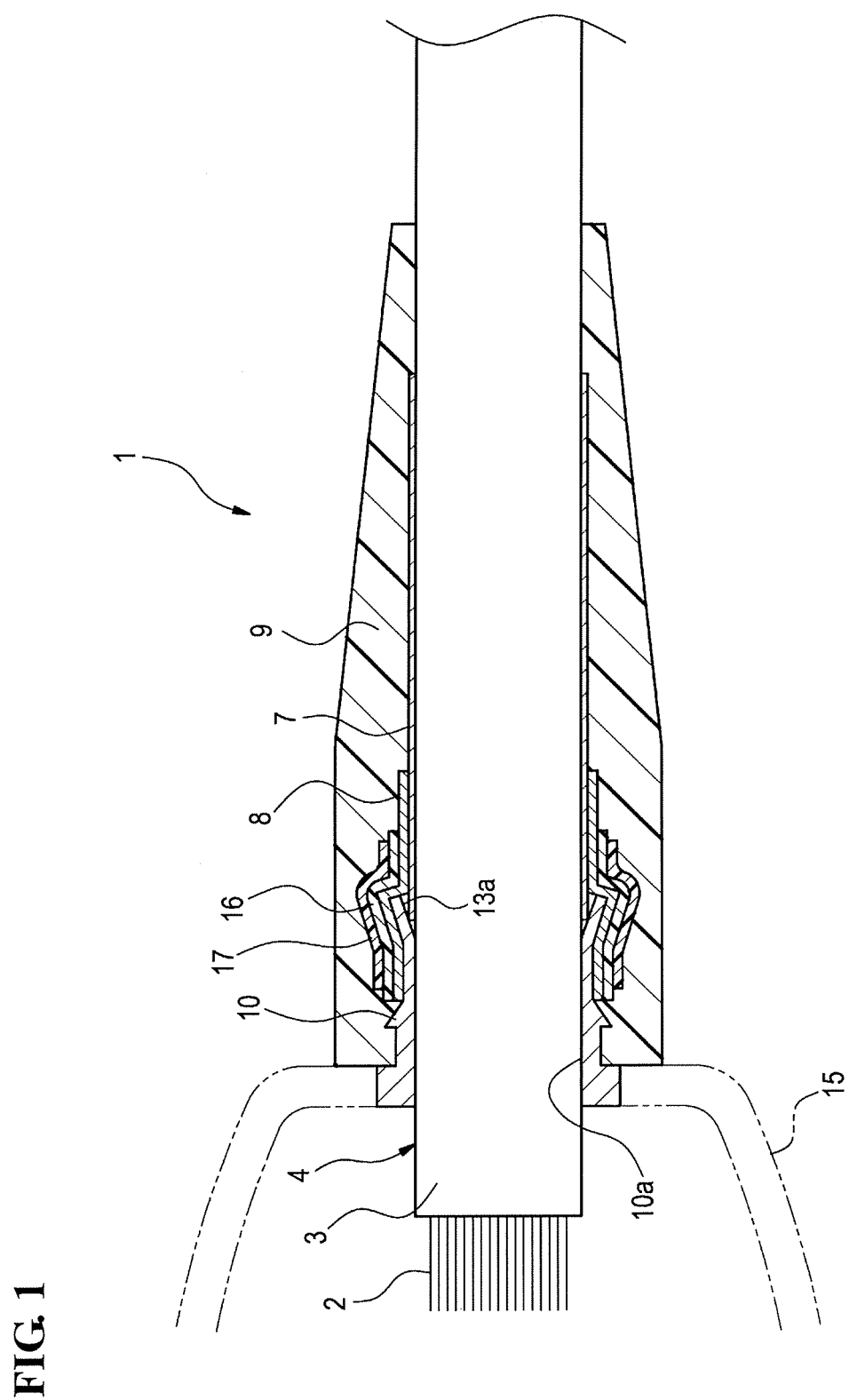
FIG. 1 is a longitudinal section of the terminal part of a cable assembly according to an embodiment of the present invention.

Hereinafter, preferred embodiments of the present invention will be described in reference to the accompanying drawings. The drawings are provided for the purpose of explaining the embodiments and are not intended to limit the scope of the invention. In the drawings, an identical mark represents the same element so that the repetition of explanation may be omitted. The dimensional ratios in the drawings are not always exact.

FIG. 1 is a longitudinal section of the terminal part of a cable assembly according to an embodiment of the present invention. A cable assembly 1 has a multi-core cable 4, a cylindrical clamp 10, two layered springs, and a rubber boot 9. The cable assembly 1 can be used as an ultrasonic probe cable. In such case, a probe case 15 is attached to the front-end side of the clamp 10 so as to cover the end of the multi-core cable 4.

Figure 2:
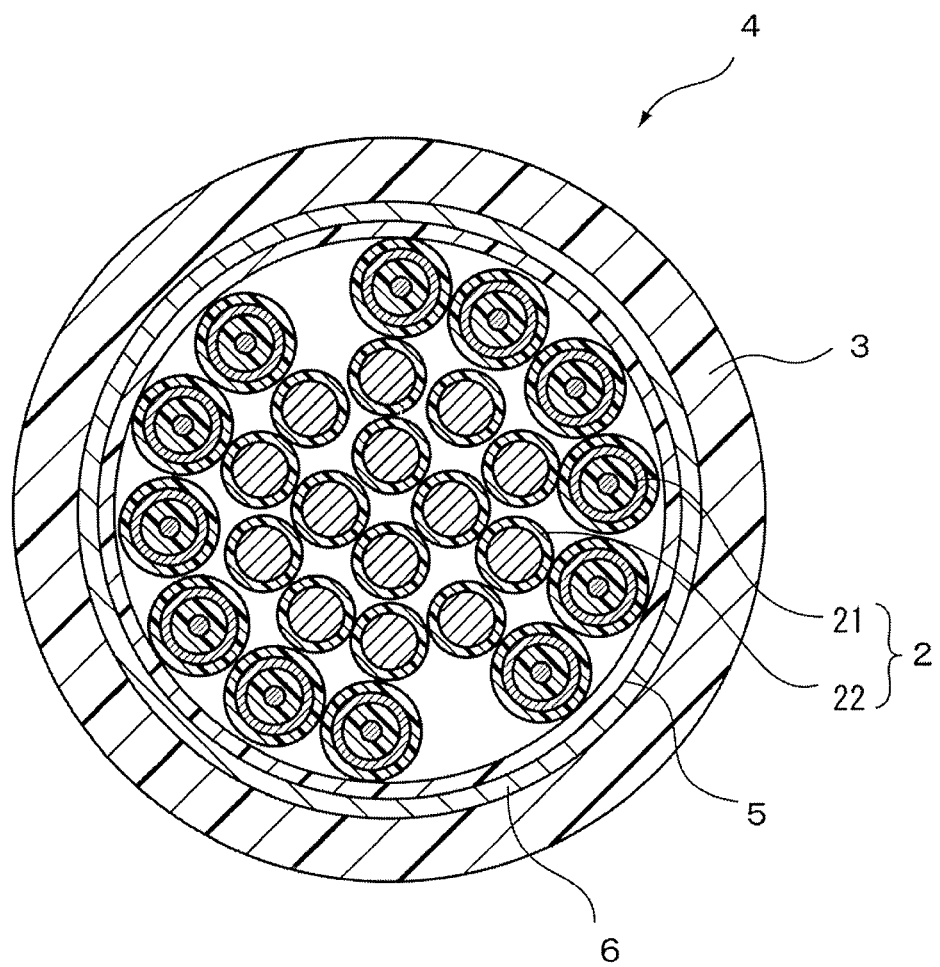
FIG. 2 is a cross-sectional view of a multi-core cable included in the cable assembly of FIG. 1.

FIG. 2 is a cross-sectional view of the multi-core cable 4. Inside the multi-core cable 4, a plurality of core wires 2 (insulated wire 21 and coaxial wire 22) are bundled, and in the named order, an overall wrapping 5, a shielding layer 6, and a sheath 3 are formed around the bundled core wires. The core wires 2 have a diameter of about 1 mm or thinner, and are either a small-diameter insulated wire 21 having a core conductor covered with a coating layer, or a small-diameter coaxial wire 22 having a core conductor, an insulation layer, a shielding layer, and a covering layer which are included in the named order from the center to the outer side. Inside the multi-core cable 4, for example, 26 core wires are bundled together, including 12 coaxial wires 22 of AWG 36 and 14 insulated wires 21 of AWG 28. The overall wrapping 5 is, for example, such that a polyethylene terephthalate (PET) tape is wrapped by longitudinally applying around the bundled core wires 2. The shielding layer 6 is, for example, formed by spirally applying a plurality of copper wires in double layers around the overall wrapping 5. The sheath 3 is made of polyvinyl chloride (PVC), for example.

As shown in FIG. 1, the sheath 3 of the multi-core cable 4 is removed at an end portion so that a plurality of core wires 2 are exposed. The end of the exposed core wires 2 is connected to a connector (not shown in the figure), which is to be connected with a connector provided on an ultrasonic detection unit inside the probe case 15. When the cable assembly 1 is used as a camera cable for an endoscope or the like, the connector of the core wires 2 is to be connected with an imaging device and the like. In the cable assembly 1, a metal clamp 10 is attached to the end portion on the core-wire exposure side (the tip side) of the multi-core cable 4. On the rear end side of the clamp 10, an inner spring 7 in which the multi-core cable 4 is inserted is provided around the sheath 3, and an outer spring 8, which is formed in a shape shorter than the inner spring 7 in terms of the cable axial direction, is arranged outside the inner spring 7.

Figure 3:
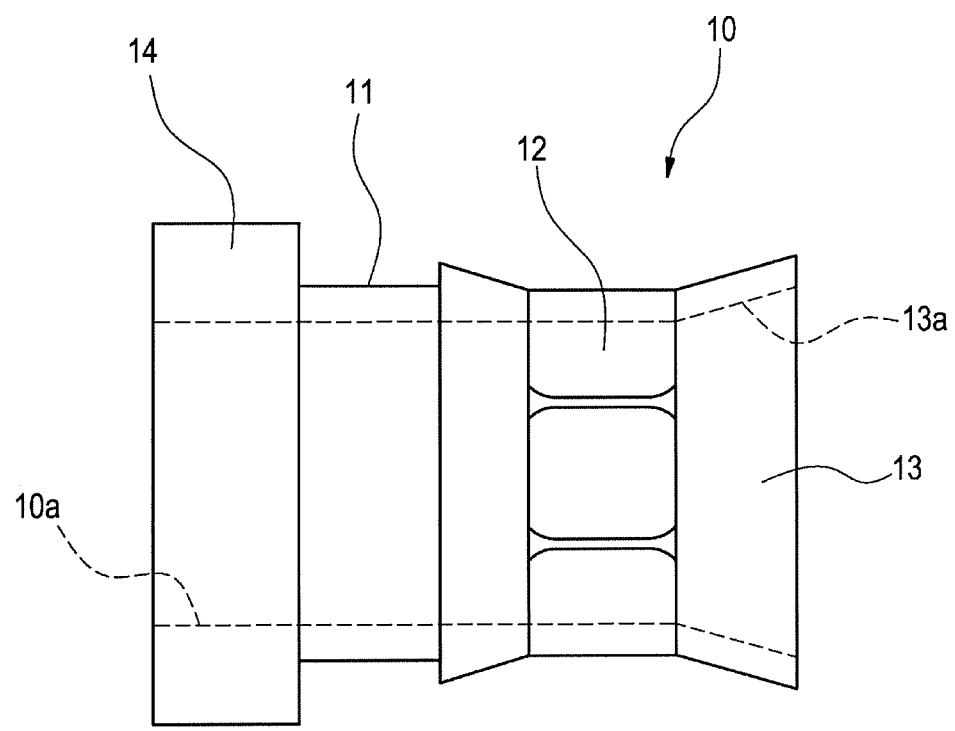
FIG. 3 is a side view of a clamp included in the cable assembly of FIG. 1.

FIG. 3 is a side view of the clamp 10. In the clamp 10, a large diameter brim portion 14 is formed on the tip side, and a groove portion 11 for fastening a rubber boot 9 is formed on the rear side of the brim portion 14. And, on the rear side of the groove portion 11, a caulking portion 12 for fixing the multi-core cable 4 by caulking after insertion of the multi-core cable 4 into an insertion hole 10a is provided. When the caulking portion 12 is attached to the multi-core cable by caulking, it exhibits, for example, a hexagonal section in terms of the outer circumference. A diameter increasing portion 13 is formed on the rear side of the caulking portion 12, that is, at the rear end portion of the clamp 10. The diameter increasing portion 13 is in a shape such that the diameter of the inner surface 13a which constitutes a part of the insertion hole 10a gradually increases as it is closer to the rear end.

The clamp 10 is made of copper, for example, so that caulking may easily be accomplished. Also, if plastic deformation by means of caulking is possible, the clamp 10 may be made of synthetic resin instead of metal. In the case where the clamp 10 is caulked in a polygonal shape, the caulking power can be applied substantially equally, without making excessive caulking, whereby the product quality upon caulking can be made more stable. As for the polygonal shape of the clamp 10, it is possible to adopt a polygonal shape of about 20 angles at maximum.

Figure 4:
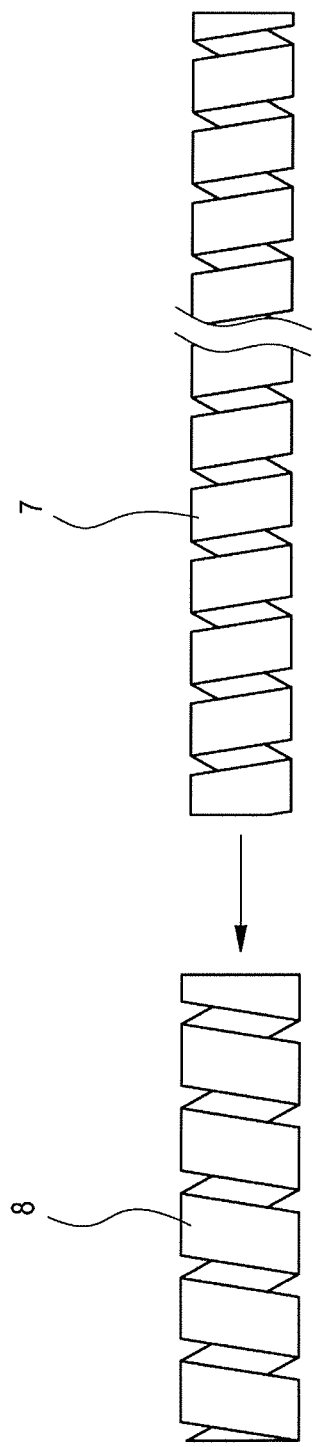
FIG. 4 is a side view of two layers of springs to be included in the cable assembly of FIG. 1.

FIG. 4 is a side view of two layers of springs to be included in the cable assembly 1. As for the two layered springs, the inner spring 7 is made by spirally transforming a thin metallic plate into a cylindrical spring, or by spirally cutting a metal cylinder so as to be a spring; and the outer spring 8 has a shape similar to the inner spring 7, but it is shorter than the inner spring 7 and has an inside diameter that is substantially equal to the outside diameter of the inner spring 7 so that it can be arranged in contact with the outer circumference of the inner spring 7. The spiral directions of the inner spring 7 and that of the outer spring 8 are opposite to each other so that the strength of the cable assembly 1 is equalized at the part where these springs are overlapped.

As shown in FIG. 1, the front (the end portion side of the multi-core cable) end portion of the inner spring 7 is placed inside the diameter increasing portion 13 of the clamp 10 and is fixed between the inner surface 13a of the clamp 10 and the sheath 3 of the multi-core cable 4. Also, the outer spring 8 is arranged such that the front end portion, which is placed over the outer circumference of the diameter increasing portion 13 of the clamp 10, is fixed to the clamp 10 by shrinking a shrinkable tube 16 that covers such end portion. The rear end portion of the outer spring 8 is arranged on the outer circumference of the inner spring 7. It is unnecessary to fix the end of the outer spring 8 at the rear end side since it does not touch the sheath 3. However, it may be fixed with a shrinkable tube or an adhesive tape so as to prevent damage of the rubber boot 9. Adhesive tapes may be used instead of shrinkable tubes 16 and 17.

The rubber boot 9 is provided so as to cover the inner spring 7 and the outer spring 8. The tip of the rubber boot 9 is fastened at the groove portion 11 of the clamp 10 so that it is prevented from moving in the longitudinal direction. Also, the inner surface at the end portion (the part which does not touch a spring) of the rubber boot 9 is attached to the sheath 3 with an adhesive.

To manufacture the cable assembly 1, first, the multi-core cable 4 is inserted in the rubber boot 9 beforehand, and subsequently inserted into shrinkable tubes 16 and 17, the inner spring 7, and the outer spring 8. Then, after insertion of the multi-core cable 4 into the clamp 10, the clamp 10 is fixed to the multi-core cable 4 by caulking the caulking portion 12 of the clamp 10. Next, the shrinkable tubes 16 and 17, the inner spring 7, the outer spring 8 are disposed by sliding to the positions shown in FIG. 1, and subsequently the inner spring 7 and the outer spring 8 are fixed by heating the shrinkable tubes 16 and 17. Lastly, the rubber boot 9 is arranged by sliding to its position shown in FIG. 1, and fixed by fastening at the groove portion 11.

The cable assembly 1 having such structure is improved in terms of bending resistance by reinforcement with the inner spring 7 and the outer spring 8 which are provided in an overlapping manner around the multi-core cable 4. Also, the rear end of the clamp 10 has the diameter increasing portion 13 formed such that the inside diameter increases by several percentage to tens of percentage as it is closer to the rear end, and accordingly the multi-core cable 4 will less suffer from interference with the rear end of the clamp 10 when it is bent. Thus, the bending angle of the core wires 2 of the multi-core cable 4 can be made moderate.

Also, at the rear end portion of the clamp 10, the inner spring 7 is sandwiched between the clamp 10 and the sheath 3 of the multi-core cable 4, so that the multi-core cable 4 is prevented from bending at the rear end portion of the clamp 10, and accordingly the bending of the core wires 2 are more effectively prevented. Furthermore, the outer spring 8 is provided outside the inner spring 7 in the rear end portion of the clamp 10 and the vicinity thereof, and consequently the reinforcement becomes stronger, thereby improving the bending resistance. The tip portion of the inner spring 7 (60 to 120 mm in length) is fixed inside the clamp 10, and moreover the tip portion of the outer spring 8 (30 to 60 mm in length) is fixed around the outer circumference of the clamp 10, and consequently the tip positions of the inner spring 7 and the outer spring 8 will not change relative to the sheath 3 when the cable bending occurs; thus they will protect the sheath 3.

As described above, the cable assembly 1 has high bending resistance and is suitable for application in medical inspection, treatment, and the like. The cable assembly 1 withstands bending applied about tens of thousands of times in the vicinity of the part where the clamp 10 is attached, and the core wires 2 are prevented from sharp bending and will not break.

Figure 5:
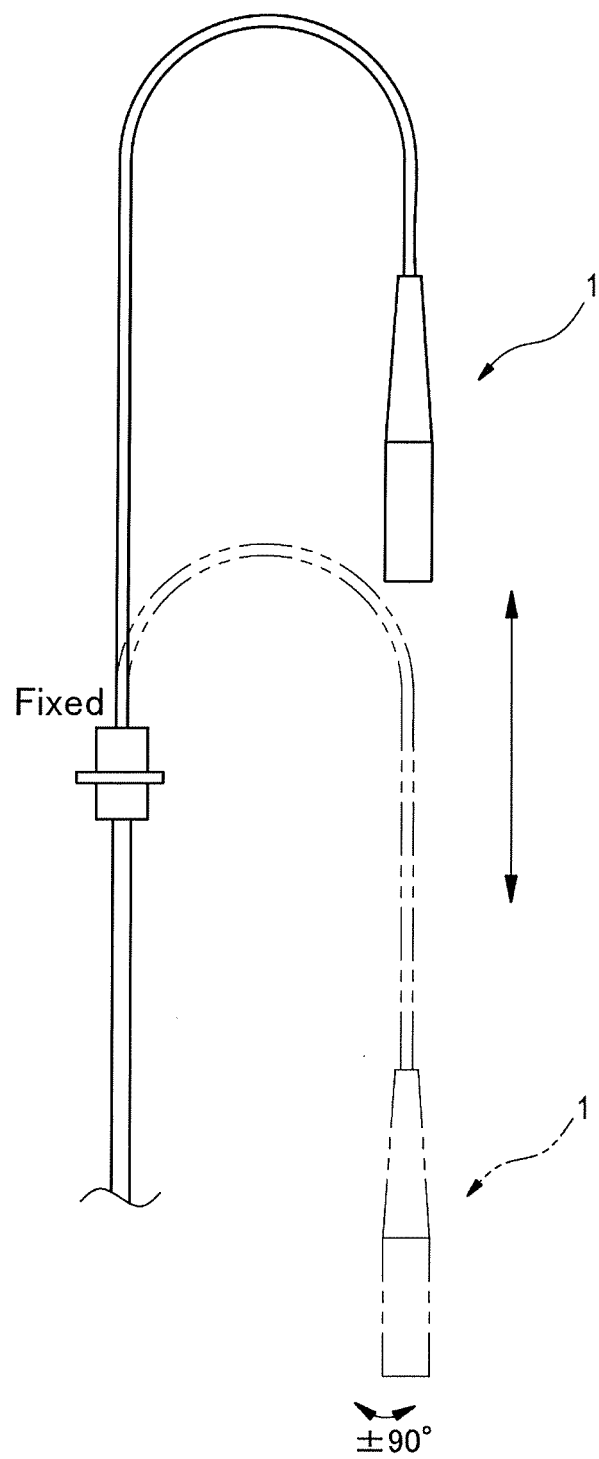
FIG. 5 is a conceptional schematic diagram of a bending test of the cable assembly.

FIG. 5 is a conceptional schematic diagram showing a bending test of the cable assembly. For example, the core wires 2 did not break even when the bending test was performed by bending repeatedly 90,000 times in a manner such that the cable assembly 1 was bent by 180° from a straight condition and the rubber boot was turned by ±90° around the axis of the cable. On the other hand, when such bending test was performed with respect to a multi-core cable in the case where a clamp whose diameter was not increased at the rear end portion was used and a rubber boot was attached by reinforcing with a wrapped polytetrafluoroethylene tape instead of a spring, a core wire was broken at the stage of bending the cable 50,000 times.

What is claimed is:

1. A cable assembly comprising a multi-core cable, a cylindrical clamp, two layers of springs including an inner spring and an outer spring, and a rubber boot, wherein the multi-core cable includes a bundled plurality of core wires having each conductor covered with an insulation, a shielding layer provided around the plurality of core wires, and a sheath formed around the shielding layer;

the cylindrical clamp is fixed by clamping the sheath at an end portion of the multi-core cable in a state where the multi-core cable is inserted in the clamp, whereas at a position opposite to a front end of the multi-core cable, the clamp has a diameter increasing portion such that the inside diameter increases as it is more distant from the front end;

the inner spring having the multi-core cable partly inserted therein is attached around the sheath on the rear side of the clamp in a manner such that the front end portion of the inner spring is fixed to the clamp in a state where it is held between the sheath and the internal circumference of the clamp;

the outer spring having a shorter length than that of the inner spring in the longitudinal direction of the multi-core cable is provided in a manner such that the front end portion of the outer spring is fixed to the outer circumference of the clamp; and the rubber boot covers the outer circumferences of the inner spring and the outer spring.

2. A cable assembly according to claim 1, wherein the clamp has, as named from the tip side, a brim portion, a groove portion, a caulking portion, and the diameter increasing portion, and the rubber boot is fastened to the groove portion.

3. A cable assembly according to claim 1, wherein the inner spring and the outer spring are formed into a cylindrical shape by transforming a thin metal plate spirally or by making a spiral slit in a circular metal cylinder, and their spiral directions are opposite to each other.

4. A cable assembly according to claim 2, wherein the inner spring and the outer spring are formed into a cylindrical shape by transforming a thin metal plate spirally or by making a spiral slit in a circular metal cylinder, and their spiral directions are opposite to each other.

* * * * *